United States Patent [19]
McKay et al.

[11] Patent Number: 5,105,024
[45] Date of Patent: Apr. 14, 1992

[54] PROCESS FOR CONCURRENTLY PRODUCING PROPYLENE AND METHYLTERTIARYBUTYL ETHER

[75] Inventors: Dwight L. McKay; Michael L. Gray, both of Bartlesville, Okla.

[73] Assignee: Phillips Petroleum Company, Bartlesville, Okla.

[21] Appl. No.: 512,169

[22] Filed: Apr. 20, 1990

[51] Int. Cl.$^5$ .............. C07C 41/06; C07C 5/32
[52] U.S. Cl. ........................ 568/697; 585/324
[58] Field of Search ............... 568/697; 585/324

[56] References Cited

U.S. PATENT DOCUMENTS

| | | | |
|---|---|---|---|
| 4,329,516 | 5/1982 | Al-Muddarris | 568/697 |
| 4,447,653 | 5/1984 | Vora | 568/697 |
| 5,558,168 | 12/1985 | Gussow et al. | 568/697 |

Primary Examiner—Howard T. Mars
Attorney, Agent, or Firm—Laney, Dougherty, Hessin & Beavers

[57] ABSTRACT

Isobutane and propane are separately charged to different catalytic dehydrogenation zones. The reaction products, including principally propylene and isobutylene, are combined, followed by separation of steam condensate, carbon dioxide and fuel gas from the mixture of effluents from the two separate dehydrogenation reaction zones. Propane and propylene are then separated from the isobutylene. The propylene product is recovered, and isobutylene is charged to an etherification reactor and there reacted with methanol to yield methyltertiarybutyl ether (MTBE). The etherification reactor effluent is fractionated to separate MTBE from n-butane and from isobutane. The latter is separated from n-butane and recycled to the isobutane dehydrogenation zone. Unreacted propane is also recovered and recycled.

8 Claims, 1 Drawing Sheet

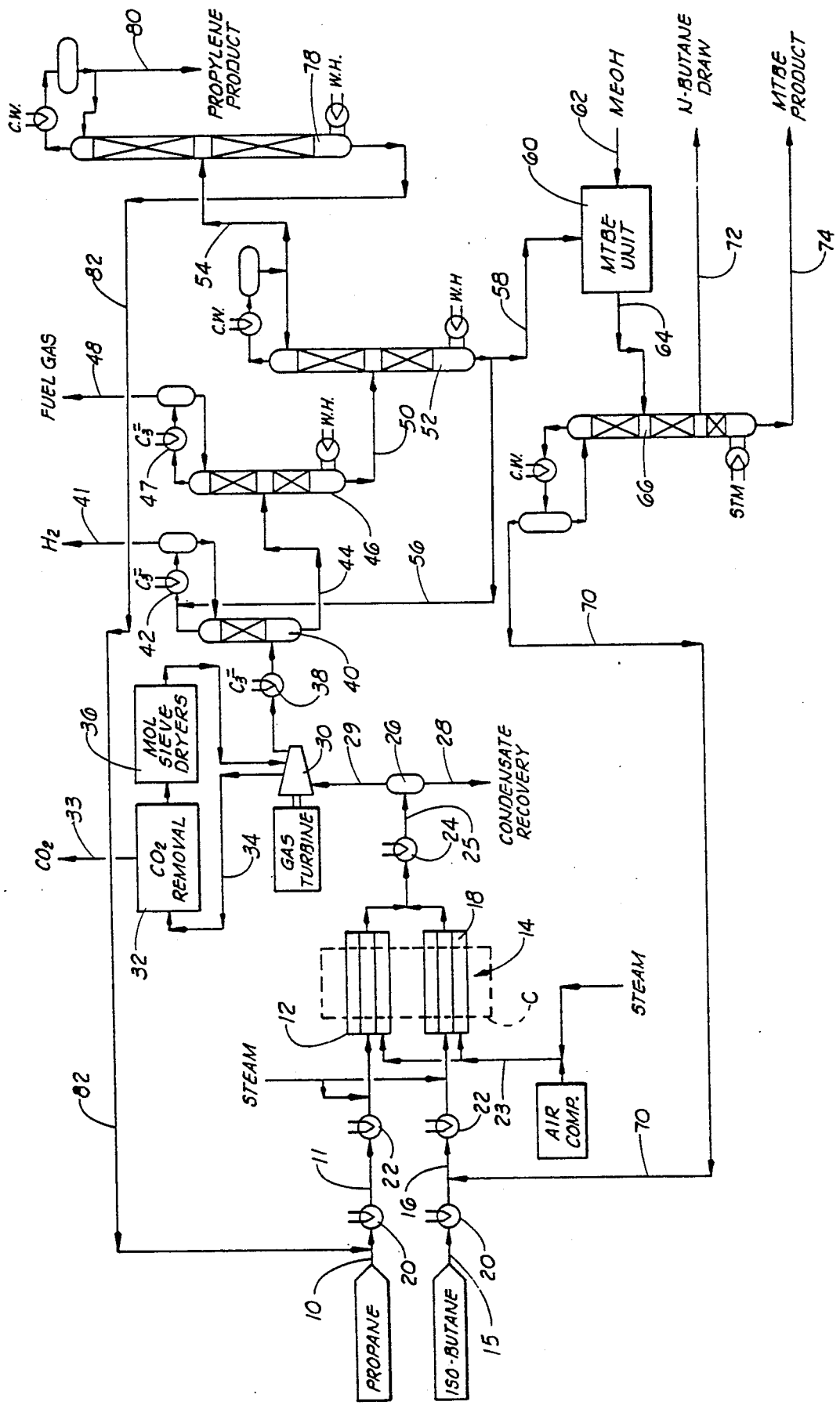

PROCESS FOR CONCURRENTLY PRODUCING PROPYLENE AND METHYLTERTIARYBUTYL ETHER

BACKGROUND OF THE INVENTION

1. Field Of The Invention

This invention relates to a process for concurrently producing propylene and methyltertiarybutyl ether using catalytic dehydrogenation and etherification reaction zones.

2. Brief Description Of The Prior Art

In U.S. Pat. No. 4,118,425, a process is disclosed for preparing the methyl ether of tertiary butanol by reacting methanol and isobutene. This general process is otherwise well known and is also disclosed in other patents. In U.S. Pat. No. 4,118,425, normal butane is isomerized to produce an isomate which contains isobutane, and normal butane. This isomate is dehydrogenated to form predominantly isobutene and normal butane by passing the isomate over a chromium-on-alumina catalyst where approximately half of the normal butane in the stream is converted to butenes. The dehydrogenate is then reacted with a water soluble alkanol, such as methanol, in the presence of an etherification catalyst. A reaction product results which contains the product ether, such as methyltertiarybutyl ether, n-butane and excess of the water soluble alcohol which has not entered into the etherification reaction. The effluent from the etherification reaction will also contain some linear butenes.

Water-soluble alcohol can be easily separated from the normal butane and from the product ether. Components of the etherification reactor effluent such as butene-1, cis-trans-butene-2, isobutane and normal butane pass through the etherification zone as inerts—that is, they are not converted to other products during etherification. The ether product is thus mixed with normal butane and isobutane.

Separation of the desired ether product from the other compounds with which it is mixed in the etherification reactor effluent can be effected by fractional distillation. The relatively heavy ether product is recovered from the bottom of the fractionation tower; the overhead from the tower includes normal butane and isobutane. The patentee states that overhead from the distillation may be recycled, or it may be withdrawn from the process, depending on the needs of the system. In either case, it does not appear that a separation of butane from isobutane is attempted, nor is there any effort made to isolate or remove linear butenes from the total effluent product from the etherification reactor. If the isobutanes are recycled, it appears from the disclosure of the patent that the n-butane is also recycled. It is indicated in this patent that it is desirable to recycle isobutane, and to include a certain amount of linear butane material in the charge stock to the dehydrogenation reactors. No concern is manifested for any build up of normal butane in the course of continuously operating the described process.

SUMMARY OF THE INVENTION

In accordance with the present invention, propane and isobutane are preferably concurrently charged through separate reactor sections or through separate furnaces in which dehydrogenation of these compounds is achieved by the use of a steam active dehydrogenation catalyst. The effluent streams from the two reactors are combined, and the combined effluent stream is then processed to separate out steam condensate, fuel gas made up of $C_2$ and lighter gases, propylene product and some unreacted propane. A separated stream containing $C_4s$, including isobutylene, isobutane and normal butane, is then charged to an etherification reactor, where the isobutylene is combined with methyl alcohol to yield methyltertiarybutyl ether. The linear $C_4s$ in the effluent from the etherification reactor are separated from the ether product in a side stream which is withdrawn from a debutanizer fractionating column which also separates the ether product as a higher boiling fraction. The unreacted isobutane which is separated as overhead from the debutanizer is then recycled to the dehydrogenation reactor.

Withdrawal of the normal butane is accomplished by a side draw from the debutanizer unit. This prevents undesirable build up of normal butane in the charge to the dehydrogenation reactor, while allowing the unreacted isobutane which has passed through the dehydrogenation reactor and through the etherification reactor to be recycled to the dehydrogenation unit.

An important advantage of the invention is to provide a system for simultaneously processing propane and isobutane feed stocks to valuable propylene and methyltertiarybutyl ether products in a cyclic reaction scheme, which, by reason of improvements residing in the removal of certain materials to prevent their undesirable build up in the recycle stream, enables the process of the invention to have an extended, trouble free operating life.

Another object of the invention is to provide a process for converting propane to propylene, and isobutane to isobutylene and the latter then to methyltertiarybutyl ether in a way such that the effluent from the initial dehydrogenation step is a combined effluent from dehydrogenation reactors to which the propane and isobutane are separately but concurrently charged. By combining the effluents, the loss of $C_3$ and $C_4$ compounds by conversion to lower value fuel gas is reduced as compared to the magnitude of such loss which would occur if the propane and isobutane were processed in completely independent systems.

Additional objects and advantages of the invention will become apparent as the following detailed description of a preferred embodiment of the invention is read in conjunction with the accompanying drawing which illustrates such preferred, embodiment.

GENERAL DESCRIPTION OF THE DRAWING

The drawing is a schematic illustration of one embodiment of the process of the invention. For purposes of simplicity and ease of understanding, many pieces of apparatus which are required for the successful operation of the process, such as pumps, compressors, temperature, pressure and flow rate monitoring and control systems, flow control valves, etc., have not been shown. This schematic representation of one embodiment of the invention is not intended to exclude from the scope of the inventive concept, those other embodiments which are expressly disclosed herein, but which result from reasonable and anticipated modifications which may be made by those skilled in the art, or are clear and readily apparent equivalents of the process units, and methodology steps.

DETAILED DESCRIPTION OF A PREFERRED EMBODIMENT OF THE INVENTION

The instant invention is directed to an improved process for producing propylene utilizing a known dehydrogenation process, and concurrently producing isobutylene by separately charging isobutane to a separate dehydrogenation zone, and then ultimately charging the products from this reaction zone, consisting primarily of isobutylene, to an etherification reactor. In the etherification reactor the isobutylene is combined with methanol to produce methyltertiarybutyl ether.

The procedure will thus be perceived to involve the concurrent dehydrogenation of propane and isobutane in separate sections of a reactor or furnace, or alternatively, in separate reactors, or separate furnaces. In either operation, the type of dehydrogenation utilized is known technology. Preferably a steam active catalyst effects the dehydrogenation of the charged compounds to yield, in the case of propane, propylene, and in the case of the isobutane charge, isobutylene. In general, such reaction is carried out at a temperature in the range of from about 900° F. to about 1,150° F., preferably from about 1,080° F. to about 1,120° F., and at a pressure in the range of from about 0 psig to about 400 psig, and preferably about 0 psig to about 300 psig. Generally, the molar ratio of steam to hydrocarbon is in the range of about 1:10 to about 25:1, preferably about 2:1 to about 15:1. The Liquid Hourly Space Velocity (LHSV) of hydrocarbon per volume of catalyst per hour is generally in the range of from about 0.5 to about 10.

The steam active dehydrogenation catalyst is broadly a Group VIII metal catalyst on a support which is repetitively regenerated. The preferred Group VIII metal is platinum. The support can be alumina, silica, magnesia, zirconia, alumina-silicates, Group II metal aluminate spinels and mixtures of such supports. Group VIII and Group II metals are so classifed in the Period Table of the Elements as set forth in *Chemical Rubber Company, Handbook of Chemistry and Physics*, 45th Edition, (1964) Page 13-2.

According to the present invention, the effluent streams emanating from each of the dehydrogenation reactors are combined, and the combined effluent flows through a single separations train. Initially, steam in the effluent is condensed and recycled to the reactor. Carbon dioxide is next removed, and then the remaining gases are dried to assure that hydrates will not form in the separations units. After drying the gases which remain following removal of carbon dioxide, a hydrogen-rich stream is preferably separated and yielded from an absorber.

The remaining stream of gases is then passed to a deethanizer fractionation unit, and the $C_2$ and lighter components are separated as a fuel gas stream. The heavier components from the de-ethanizer are passed to a depropanizer fractionator where the heavier $C_4$ stream is removed from the bottom of the unit, and the $C_3$ stream is taken overhead.

The $C_3$ stream is fractionated to yield the desired propylene product and a propane stream which is recycled to the propane dehydrogenation reactor. A part of the $C_4$ bottoms stream from the de-propanizer is preferably recycled to the absorber unit used for removing the hydrogen-rich stream. The remainder of the $C_4$ stream is combined with a lower alcohol, preferably methanol, and is fed to an etherification reactor. In the etherification reactor, the isobutylene in the $C_4$ stream and the methanol react to form methyltertiarybutyl ether. The product stream from the etherification reactor contains methyltertiarybutyl ether as its major component, but it also contains linear, branched, saturated and unsaturated $C_4$s which pass through the etherification reactor. The isobutane in the etherification reactor effluent is, of course, a desirable hydrocarbon for recycling to the dehydrogenation reactor which functions to produce the isobutylene. The normal butane, however, constitutes an undesirable hydrocarbon in the recycle stream, and it is therefore advantageous to remove this species in order to prevent its build up, conversion to butadiene and ultimate coking of the dehydrogenation catalyst.

Removal of normal butane from methyltertiarybutyl ether is effected by fractionation in which the entire effluent mixture is charged to a de-butanizer fractionating column. Here the normal butane and some of the linear butenes and butadiene are removed as a side draw from the column. The ether product is withdrawn as the bottom or heavier fraction, and the isobutane is taken off as overhead, and is recycled to the hydrogenation reactor.

A better understanding of the invention will be obtained by reference to the accompanying drawing which shows a schematic arrangement of apparatus and flow diagram representing a preferred embodiment of the invention.

Referring to the drawing, a propane-containing stream is introduced via a conduit 10. Depending upon the source of the propane, this stream will usually contain small amounts of $C_2$ and $C_4$. When the process is fully on stream, a $C_3$ recycle stream is introduced to the propane make-up entering the process via the line 10, and the merged streams are passed through line 11. The propane-containing stream is charged via the conduit 11 to a first section 12 of a dehydrogenation catalytic reactor designated generally by reference numeral 14. Concurrently, a stream containing predominantly isobutane, but containing also minor amounts of normal butane and a small amount of propane, is charged to the process via a conduit 15. After merging with an isobutane recycle stream, introduced via a conduit 70, the isobutane stream moves through conduit 16 to a second section 18 of the dehydrogenation catalytic reactor 14. As indicated by the dashed line block or rectangle C, the reactor sections 12 and 18 may actually be two separated, independently operating sections of the same reactor 14 in which the propane and the isobutane are independently reacted.

Enroute to the sections 12 and 18, the propane charge stock and the isobutane stream are each subjected to feed vaporization in units 20 and then preheat by units 22 as illustrated in the drawing. The dehydrogenation reactor sections 12 and 18 are conventionally constructed, as hereinafter described. A source of steam is charged continuously to each reactor via conduit 23. A stream of compressed air is added to the steam during catalyst regeneration.

Actually, eight dehydrogenation reactors or reactor sections are typically used to accomplish the dehydrogenation functions shown as being generically effected in each of the reactor sections 12 and 18. That is, eight reactors are typically used to process each individual feedstock. At any time, seven reactors will be dehydrogenating the hydrocarbon feedstock while one reactor will be concurrently undergoing regeneration. In small plants, one reactor operating on a blocked out basis is generally sufficient. In general, reactor cycle times are seven hours on process, and one hour on regeneration. In some situations, longer cycle times are possible.

Each regeneration has two phases. Initially air is admitted to the regeneration steam flow in a limited quantity that is controlled to limit the temperature rise in the catalyst in the bed. In the initial phase all the oxygen added reacts with the carbon and hydrogen deposited on the catalyst as coke during the on-line dehydrogenation part of the cycle.

In the second phase of regeneration, the quantity of air added to the regeneration steam is increased in order to give complete recovery of catalyst activity in a short period of time.

At the end of each regeneration, air is backed out of the steam. After purging with steam, the flow of hydrocarbon to the reactor is restarted. In similar fashion, the hydrocarbon flow to the next reactor tube to be regenerated is gradually reduced. After a short period, air is admitted to the regeneration steam flow to begin catalyst regeneration for the next process cycle.

The regeneration off gas may be combined with process gases and then removed in the separation section of the plant, or the regeneration off gas may be isolated from process gases, using an appropriate arrangement of valves.

The optimum conditions for dehydrogenation of propane to propylene in the reactor section 12, and isobutane to isobutylene in the reactor section 18 are different. Processing each feedstock individually at optimum dehydrogenation conditions for that feedstock improves the economics of the overall process. The dehydrogenation reaction occurring in the reactor section 12 yields principally propylene, and byproducts produced in the propane dehydrogenation reactor further include methane, ethane, ethylene, $C_5+$ hydrocarbon (trace), carbon monoxide, carbon dioxide, coke and hydrogen. Some water is consumed in the reactor. The dehydrogenation of the isobutane in the reactor section 18 yields predominantly isobutylene. By-products produced in the isobutane dehydrogenation reactor include methane, ethane, ethylene, propylene, propane, n-butane, butene-1, t-butene-2, c-butene-2, butadiene, $C_5+$ hydrocarbons (trace), carbon monoxide, carbon dioxide, coke and hydrogen. Some water is consumed in the reactor.

The product streams or discharged effluent from reactor sections 12 and 18 are combined into a single stream, which, after passing through a heat recovery unit 24, passes through a line 25 to a knockout drum 26 in which steam condensate is recovered. The steam condensate is recycled as indicated by the condensate recovery line 28. After removal of the condensate, the combined effluent passes through a conduit 29 to a gas turbine 30 which charges the gas through a carbon dioxide removal unit 32 which functions to remove carbon dioxide in a stream 33 from the mixture of gases in stream 34. The gaseous mixture is then passed through a molecular sieve dryer 36 where the remaining gases are dried to assure that hydrates will not form in the separation units to which the gaseous mixture is to be subsequently passed. The gases are next passed through a propylene refrigeration chiller unit 38 to an absorber 40. The absorber 40 functions to remove a hydrogen rich stream 41 from the gaseous mixture after the overhead from the absorber has been passed through a propylene refrigeration unit 42 to retain low boiling gases in the stream while removing hydrogen.

The gases remaining after hydrogen removal are next passed from the absorber 40 through a conduit 44 to a deethanizer fractionating column 46. Here process waste heat is used to fractionate the gases so that, after passing through a propylene refrigeration unit 47, $C_2$ and lighter gases, constituting a fuel gas, are taken off as overhead through the conduit 48. The high boiling components of the gaseous mixture are removed at the bottom of the deethanizer 46 via the conduit 50 and are charged to a depropanizer unit 52.

The de-propanizer unit 52 effectively removes $C_3$ compounds as overhead via the conduit 54, while withdrawing the higher boiling $C_4$ compounds from the lower part of the column. A portion of the $C_4$ stream is recycled to the absorber 40 via a conduit 56. The major portion of the $C_4$ stream is directed via the conduit 58 to an etherification reactor 60 in which methyltertiarybutyl ether (MTBE) is produced. The ether is produced in the etherification unit 60 by reaction of isobutylene from the feed conduit 58 with methyl alcohol charged to the etherification unit via the conduit 62.

The products from the etherification unit 60 include predominantly the methyltertiarybutyl ether product principally sought, but also include significant amounts of normal butane, isobutane and normal butenes. This mixture is discharged from the etherification unit 60 through the conduit 64 to a debutanizer fractionation column 66. In the debutanizer fractionation column 66, isobutane, which is a relatively low boiling component of the mixture, is taken off as overhead from the column and is recycled via a conduit 70 to the isobutane charge material directed to the dehydrogenation reactor via the conduit 16. A side draw stream 72 from the de-butanizer fractionator 66 functions to remove a major portion of the normal butane and normal butenes from the etherification reactor effluent. The highest boiling component of the mixture discharged from the etherification unit is, of course, the methyltertiarybutyl ether which is removed via the conduit 74 from the bottom of the de-butanizer column 66.

The $C_3$ stream which was removed to the de-propanizer fractionator column 52 and passed through the conduit 54 enters a fractionating column which functions as a propane propylene splitter 78. The lower boiling propylene is removed from the splitter as overhead, and is recovered as product via conduit 80. The relatively heavier propane is recovered from the bottom of the splitter 78 and is recycled through conduit 82 to the conduit 10 through which propane is charged to the dehydrogenation reactor 12.

The details of construction of the etherification reactor and the type of catalyst and operating conditions which are used therein for producing the methyltertiarybutyl ether, constituting a valuable additive to high octane gasoline, are well understood in the art and are discussed in detail in U.S. Pat. Nos. 4,118,425, which patent is incorporated herein by reference. Details thereof are not here described, since such are well known to those skilled in the art.

EXAMPLE I

In this example, typical operations of units illustrated in the drawing are set forth. The reference numerals, used in the previous description to refer to certain conduits and reactor units in the drawing, and to allude to the fact that certain materials are moved through those conduits from one unit to another in the process flow diagram are now used in Table I to show the balance of materials through the process.

TABLE I

| Component | 10 C$_3$ Feed Lb/hr | 15 i-C$_4$ Feed Lb/hr | 82 C$_3$ Recycle Lb/hr | 70 i-C$_4$ Recycle Lb/hr | 25 Reactor Prod. Lb/hr | 33 CO$_2$ Vent Lb/hr | 41 H$_2$ Prod. Lb/hr | 48 Fuel Lb/hr | 80 C$_3$= Prod. Lb/hr | 58 MTBE Feed Lb/hr | 62 MeOH Makeup Lb/hr | 72 Heavy Prod. Lb/hr | 74 MTBE Prod. Lb/hr |
|---|---|---|---|---|---|---|---|---|---|---|---|---|---|
| H$_2$ | 0 | 0 | 0 | 0 | 13,017 | 0 | 12,747 | .270 | 0 | 0 | 0 | 0 | 0 |
| N$_2$ | 0 | 0 | 0 | 0 | 14,697 | 0 | 13,709 | 988 | 0 | 0 | 0 | 0 | 0 |
| O$_2$ | 0 | 0 | 0 | 0 | 2,890 | 0 | 2,460 | 430 | 0 | 0 | 0 | 0 | 0 |
| CO | 0 | 0 | 0 | 0 | 636 | 0 | 576 | 60 | 0 | 0 | 0 | 0 | 0 |
| CO$_2$ | 0 | 0 | 0 | 0 | 35,432 | 35,078 | 118 | 236 | 0 | 0 | 0 | 0 | 0 |
| C$_1$ | 0 | 0 | 0 | 0 | 7,409 | 0 | 5,426 | 1,983 | 0 | 0 | 0 | 0 | 0 |
| C$_2$'s | 822 | 0 | 0 | 0 | 6,522 | 0 | 1,064 | 5,358 | 100 | 0 | 0 | 0 | 0 |
| C$_3$= | 0 | 0 | 964 | 394 | 66,862 | 0 | 669 | 1,687 | 63,148 | 394 | 0 | 0 | 0 |
| C$_3$ | 78,917 | 1,931 | 117,375 | 3,613 | 127,390 | 0 | 494 | 767 | 5,141 | 3,613 | 0 | 0 | 0 |
| i-C$_4$ | 2,466 | 187,346 | 11,483 | 200,187 | 222,520 | 0 | 3,102 | 0 | 0 | 207,935 | 0 | 7,748 | 0 |
| i-C$_4$= | 0 | 0 | 2,902 | 5,834 | 159,256 | 0 | 1,822 | 0 | 0 | 154,531 | 0 | 316 | 0 |
| n-C$_4$ | 0 | 3,863 | 18 | 5,150 | 10,409 | 0 | 92 | 0 | 0 | 10,299 | 0 | 5,150 | 0 |
| n-C$_4$= | 0 | 0 | 41 | 4,435 | 7,064 | 0 | 68 | 0 | 0 | 6,955 | 0 | 2,520 | 0 |
| C$_4$== | 0 | 0 | 5 | 216 | 441 | 0 | 5 | 0 | 0 | 431 | 0 | 216 | 0 |
| C$_5$'s | 0 | 0 | 0 | 2 | 225 | 0 | 0 | 0 | 0 | 224 | 0 | 20 | 201 |
| MTBE | 0 | 0 | 0 | 0 | 0 | 0 | 0 | 0 | 0 | 0 | 0 | 0 | 230,915 |
| Di-iC$_4$= | 0 | 0 | 0 | 0 | 0 | 0 | 0 | 0 | 0 | 0 | 0 | 0 | 604 |
| C$_4$OH | 0 | 0 | 0 | 0 | 0 | 0 | 0 | 0 | 0 | 0 | 0 | 0 | 790 |
| MeOH | 0 | 0 | 0 | 0 | 0 | 0 | 0 | 0 | 0 | 0 | 83,984 | 0 | 14 |
| H$_2$O | 0 | 0 | 0 | 0 | 881,840 | 0 | 0 | 0 | 0 | 0 | 143 | 0 | 0 |
| Total | 82,205 | 193,140 | 132,788 | 219,831 | 1,556,609 | 35,078 | 42,352 | 11,779 | 68,389 | 384,383 | 84,127 | 15,970 | 232,524 |

From the foregoing description and accompanying drawing, and the described typical operation and use of the process of the present invention, it will be perceived that the invention provides a novel intercooperation of certain plant operations which optimize the concurrent production of propylene and methyltertiarybutyl ether, a product highly useful as an octane enhancer.

It will be understood that some variations from the precise form of the preferred embodiment shown herein will clearly be operative, and will still allow the advantages and benefits of the described process to be realized. Examples of this type of variation from the described preferred embodiment would include eliminating the step of removal of the hydrogen rich stream from the fuel gas stream, and varying the amounts of the C$_4$ stream recycled to the absorber. Changes of this character, as well as many others, can be made in the described process without departure from the basic principles of the invention, and such changes are intended to be considered as within the spirit and scope of the invention when the appended claims are accorded a reasonably broad interpretation.

What is claimed is:

1. A process for producing propylene and methyltertiarybutyl ether comprising:

concurrently charging a stream containing predominantly propane, and a stream containing predominantly isobutane in parallel to separate dehydrogenation reaction zones to form a first effluent stream containing predominantly propylene and a second effluent stream containing predominantly isobutylene;

combining the first and second effluent streams;

removing carbon dioxide and C$_2$ hydrocarbons and lighter gaseous components from the combined effluent streams to leave a first residual stream containing predominantly C$_3$ and C$_4$ paraffinic and olefinic hydrocarbons;

removing propylene and propane from said first residual stream;

passing at least the major portion of the C$_4$ paraffinic and olefinic hydrocarbons, in said first residual stream to an etherification reactor;

reacting isobutylene with methanol in said etherification reactor;

removing an etherification reaction effluent stream from said etherification reactor with said stream containing at least some n-butane and some isobutane, in addition to methyltertiarybutyl ether;

fractionating the effluent from the etherification reactor to separate n-butane, methyltertiarybutyl ether and isobutane from each other; then recycling the isobutane to the dehydrogenation reactor receiving the isobutane charge stock.

2. A process as defined in claim 1 and further characterized as including the steps of:

separating propane from the propylene removed from said first residual stream; and recycling the separated propane to the dehydrogenation reaction zone receiving the propane charge stock.

3. A process as defined in claim 1 wherein each of the dehydrogenation reaction zones contains a steam active catalyst comprised of a Group VIII metal supported on a support which is selected from the group consisting of alumina, silica, magnesia, zirconia, alumina-silicates, Group II metal aluminate spinels and mixtures of such supports.

4. A process as defined in claim 3 and further characterized as including the steps of:

separating propane from the propylene removed from said first residual stream; and recycling the separated propane to the dehydrogenation reaction zone receiving the propane charge stock.

5. A process for producing propylene and alkyltertiarybutyl ether comprising:

concurrently charging a stream containing predominantly propane and a stream containing predominantly isobutane to separate dehydrogenation reaction zones to form a first effluent stream containing predominantly propylene and a second effluent stream containing predominantly isobutylene;

combining the first and second effluent stream;

removing carbon dioxide, hydrogen, methane, ethane and ethylene from the combined effluent streams to leave a first residual stream comprising $C_3$ and $C_4$ paraffinic and olefinic hydrocarbons;

removing propylene and propane from said first residual stream;

separating the propane from the propylene removed from said first residual stream;

passing to an etherification reactor at least a major portion of the $C_4$ paraffinic and olefinic hydrocarbons, including isobutylene, contained in said first residual stream after removal of propylene and propane therefrom;

reacting isobutylene with a lower alkanol containing from 1 to 3 carbon atoms in said etherification reactor;

removing an etherification reaction effluent stream from said etherification reactor, with said effluent stream containing at least n-butane and isobutane, in addition to alkyltertiarybutyl ether linear butenes and butadiene;

separating by fractional distillation in a fractional distillation column, the etherification reaction effluent steam into an overhead stream, a major portion of which is isobutane, a bottoms product consisting essentially of alkyltertiarybutyl ether, and at least one side draw stream which comprises n-butane and linear butenes withdrawn from the side of the fractional distillation column.

6. A process as defined in claim 5 wherein said dehydrogenation is effected by the use of a steam active dehydrogenation catalyst.

7. A process as defined in claim 5 wherein each of the dehydrogenation reaction zones contains a steam active catalyst comprised of a Group VIII metal supported on a support which is selected from the Group consisting of alumina, silica, magnesia, zirconia, alumina-silicates, Group II metal aluminate spinels and mixtures of such supports.

8. A process as defined in claim 5 wherein the dehydrogenation reactor is operated at a temperature of from about 900° F. to about 1,150° F., and at a pressure of from about 0 psig to about 400 psig.

* * * * *

UNITED STATES PATENT AND TRADEMARK OFFICE
CERTIFICATE OF CORRECTION

PATENT NO. : 5,105,024
DATED : April 14, 1992
INVENTOR(S) : Dwight L. McKay and Michael L. Gray It is certified that error appears in the above-identified patent and that said Letters Patent is hereby corrected as shown below:

Title page item (56):

Delete Patent Number "5,558,168" to Gussow et. al. and insert -4,558,168- to Gussow et. al.

In Column 3, line 55, delete "deethanizer" and insert -de-ethanizer-.
In Column 3, line 58, delete "depropanizer" and insert -de-propanizer-.
In Column 5, line 34, delete "byproducts" and insert -by-products-.
In Column 6, line 3, delete "deethanizer" and insert -de-ethanizer-.
In Column 6, line 9, delete "deethanizer" and insert -de-ethanizer-.
In Column 6, line 10, delete "depropanizer" and insert -de-propanizer-.
In Column 6, line 44, delete "propanepropylene" and insert -propane-propylene-.

Signed and Sealed this

Fifteenth Day of June, 1993

Attest:

MICHAEL K. KIRK

Attesting Officer    Acting Commissioner of Patents and Trademarks